(12) United States Patent
Scheer et al.

(10) Patent No.: US 6,833,028 B1
(45) Date of Patent: Dec. 21, 2004

(54) PARTICLE DEPOSITION SYSTEM WITH ENHANCED SPEED AND DIAMETER ACCURACY

(75) Inventors: Craig A. Scheer, North Attleboro, MA (US); John C. Stover, North Attleboro, MA (US)

(73) Assignee: The Scatter Works Inc., Tucson, AZ (US)

( * ) Notice: Subject to any disclaimer, the term of this patent is extended or adjusted under 35 U.S.C. 154(b) by 0 days.

(21) Appl. No.: 10/074,354

(22) Filed: Feb. 11, 2002

Related U.S. Application Data
(60) Provisional application No. 60/267,613, filed on Feb. 9, 2001.

(51) Int. Cl.[7] ........................... B05C 15/00; B05C 19/00
(52) U.S. Cl. ....................... 118/309; 118/308; 118/302; 118/693
(58) Field of Search ................................ 118/308, 309, 118/302, 693, 319, 320; 427/99, 585, 294

(56) References Cited

U.S. PATENT DOCUMENTS 4,928,537 A * 5/1990 Liu et al. .................. 73/863.86
6,136,725 A * 10/2000 Loan et al. .................. 438/758
2002/0100416 A1 * 8/2002 Sun et al. .................... 118/693

* cited by examiner

Primary Examiner—Melvin C. Mayes
Assistant Examiner—Yewebdar Tadesse
(74) Attorney, Agent, or Firm—Martine & Penilla, LLP (57) ABSTRACT

In a method for depositing particles onto a substrate a flow of gas containing particles is provided along a flow path that bypasses a deposition chamber. The flow path may direct the flow of the gas containing the particles to a vacuum. To deposit particles onto a substrate in the deposition chamber, the flow path of the gas containing the particles is diverted into the deposition chamber so that particles are deposited onto the substrate. After a desired amount of particles have been deposited onto the substrate, the flow path of the flow of the gas containing the particles is changed to the flow path that bypasses the deposition chamber. A particle deposition system and a method for maintaining particle diameter during deposition of particles onto a substrate also are described.

15 Claims, 5 Drawing Sheets

PARTICLE DEPOSITION SYSTEM WITH ENHANCED SPEED AND DIAMETER ACCURACY

CLAIM FOR PRIORITY

This application claims priority under 35 U.S.C. § 119(e) from U.S. Provisional Patent Application No. 60/267,613, filed Feb. 9, 2001, and entitled "Particle Deposition System with Enhanced Speed and Diameter Accuracy." The disclosure of this provisional application is incorporated herein by reference.

BACKGROUND OF THE INVENTION

The present invention relates generally to particle deposition and, more particularly, to a system and methods for efficiently depositing small particles on substrates.

Particle scanners are used to detect contamination on the surfaces of semiconductor wafers, computer disks, flat panel display glass, and other industrial substrates that may be sensitive to contamination. In general, these scanners operate by sensing light scattered by particles as a laser is scanned over the substrate surface. To calibrate these scanners, particles of a known size and known diameter distribution are used. The particles typically used in scanner calibration are polystyrene latex (PSL) spheres. To create a sample for use in scanner calibration, a particle deposition system is used to deposit a known amount of PSL spheres having a known particle size and a known diameter distribution onto the surface of the sample. During the deposition process, it is important that the particle deposition system does not introduce other contamination onto the sample surface.

Known particle deposition systems typically atomize a suspension of particles, e.g., PSL spheres, in clean water (or other fluid) to form a spray in a flow of clean air. After the particles dry, they are either led directly to the sample or may pass through any of several devices to control or monitor flow rates and electrically charge or discharge the particles. One common technique is to pass the particle flow through a differential mobility analyzer (DMA), which passes only a selected band of charged particle diameters through a narrow slit in a rod. An electric field draws the charged particles sideways through the clean, laminar airflow toward the rod. The smaller particles are drawn through the airflow more easily and therefore reach the rod before larger particles. By adjusting the electric field, the particle diameter that passes the slit an be selected. Control of the particle diameter selection process depends on the temperature and flow parameters in the system as well as the voltage controlling the electric field.

It has recently become more important to control precisely the particle diameter selection process to satisfy the semiconductor industry's need for more precise information regarding the true size of the particles being deposited. Commercially available particle deposition systems do not adequately monitor all of the parameters needed to obtain long-term control of the DMA. Consequently, these systems suffer from an unwanted variation in the relationship between the particle diameter passing the slit and the applied control voltage.

U.S. Pat. No. 5,534,309 to Liu discloses a method and apparatus for depositing particles on a semiconductor wafer. The disclosed method requires that a purging step be conducted to remove unwanted particles from the deposition chamber before the wafer is placed in the chamber. Another purging step is conducted at the end of each deposition before the wafer is removed from the chamber. These purging steps require that the wafer be removed from the deposition chamber at the end of each deposition. Thus, the production of sample wafers having multiple spot depositions thereon requires that the wafers must be moved into and out of the deposition chamber repeatedly. This frequent handling of the wafers significantly slows the production of sample wafers having multiple spot depositions. In addition, it also may introduce the wafers to contamination, which is undesirable in clean room operations.

In view of the foregoing, there is a need for a particle deposition system that enables the size of the particles being deposited to be precisely controlled and that reduces the time required to produce standards, e.g., sample wafers for use in scanner calibration.

SUMMARY OF THE INVENTION

Broadly speaking, the present invention fills this need by providing a particle deposition system that controls the flow of gas containing particles into a deposition chamber so that unwanted particles do not enter the deposition chamber. The particle deposition system also monitors the flow of the gas containing the particles so that the deposited particle diameter remains substantially constant during the deposition process.

In accordance with one aspect of the invention, a method for depositing particles onto a substrate is provided. In this method, a flow of gas containing particles is provided along a flow path that bypasses a deposition chamber. To deposit particles onto a substrate in the deposition chamber, the flow path of the gas containing the particles is changed so that the flow of the gas containing the particles causes particles to be deposited onto the substrate. After a desired amount of particles have been deposited onto the substrate, the flow path of the flow of the gas containing the particles is changed to the flow path that bypasses the deposition chamber.

In one embodiment, the flow of the gas containing the particles flows into a vacuum that is coupled in flow communication with the deposition chamber. In this embodiment, the vacuum is configured to prevent the flow of the gas containing the particles from entering the deposition chamber without drawing any significant amount of air from the deposition chamber. In one embodiment, the flow of the gas containing the particles is diverted from the vacuum to the deposition chamber by interrupting the flow communication between the vacuum and the flow of the gas containing the particles.

In another embodiment, particles are deposited onto the substrate in accordance with a first set of deposition parameters. Thereafter, without removing the substrate from the deposition chamber, particles are deposited onto the substrate using a second set of deposition parameters. In one embodiment, particles having the same particle size are deposited in different spot locations on the substrate. In another embodiment, particles having different particle sizes are deposited in different spot locations on the substrate.

In accordance with another aspect of the invention, a method for maintaining particle diameter during deposition of particles onto a substrate is provided. In this method, gases are flowed into a differential mobility analyzer (DMA) having a slit for passing particles therethrough. At least one of the gases flowed into the DMA contains particles. The gases flowing into and out of the DMA are monitored, and periodic adjustments are made to the voltage applied to the DMA so that a particle size diameter passed through the slit remains substantially constant during the deposition process.

In one embodiment, the monitoring of the flows into and out of the DMA includes measuring the pressure differential across orifices located before and after the DMA.

In accordance with yet another aspect of the invention, a particle deposition system is provided. In one embodiment, the particle deposition system includes a deposition chamber having an inlet and a conduit coupled to this inlet. The conduit, which has a first branch and a second branch, is in flow communication with a source of gas containing particles. A particle counter is disposed in the first branch of the conduit and an orifice is disposed in the second branch of the conduit. A vacuum is coupled in flow communication with the first and second branches of the conduit.

In another embodiment, the particle deposition system includes an atomizer for providing a flow of gas containing particles. A flow control device is coupled in flow communication with the atomizer, and a differential mobility analyzer (DMA) is coupled in flow communication with the flow control device. A deposition chamber is coupled in flow communication with the flow control device and the DMA. When the particles in the flow of the gas containing the particles are to be filtered by the DMA, the flow control device directs the flow of the gas containing the particles toward the DMA. When the particles in the flow of the gas containing the particles are not to be filtered by the DMA, the flow control device directs the flow of the gas containing the particles toward the deposition chamber.

The present invention advantageously enables particles having a constant particle diameter to be deposited onto a substrate in a deposition chamber without introducing unwanted particles in the deposition chamber. This avoids the need to purge the deposition chamber between depositions. Consequently, multiple depositions can be made on a substrate without removing the substrate from the deposition chamber. By minimizing the handling of the substrate required for deposition, the present invention significantly decreases the time required to produce standards having multiple depositions thereon. It also minimizes the opportunity for contamination to be introduced onto the substrate during the deposition process.

It is to be understood that the foregoing general description and the following detailed description are exemplary and explanatory only and are not restrictive of the invention, as claimed.

BRIEF DESCRIPTION OF THE DRAWINGS

The accompanying drawings, which are incorporated in and constitute part of this specification, illustrate exemplary embodiments of the invention and together with the description serve to explain the principles of the invention.

DETAILED DESCRIPTION OF EXEMPLARY EMBODIMENTS

Several exemplary embodiments of the invention will now be described in detail with reference to the accompanying drawings.

Figure 1:
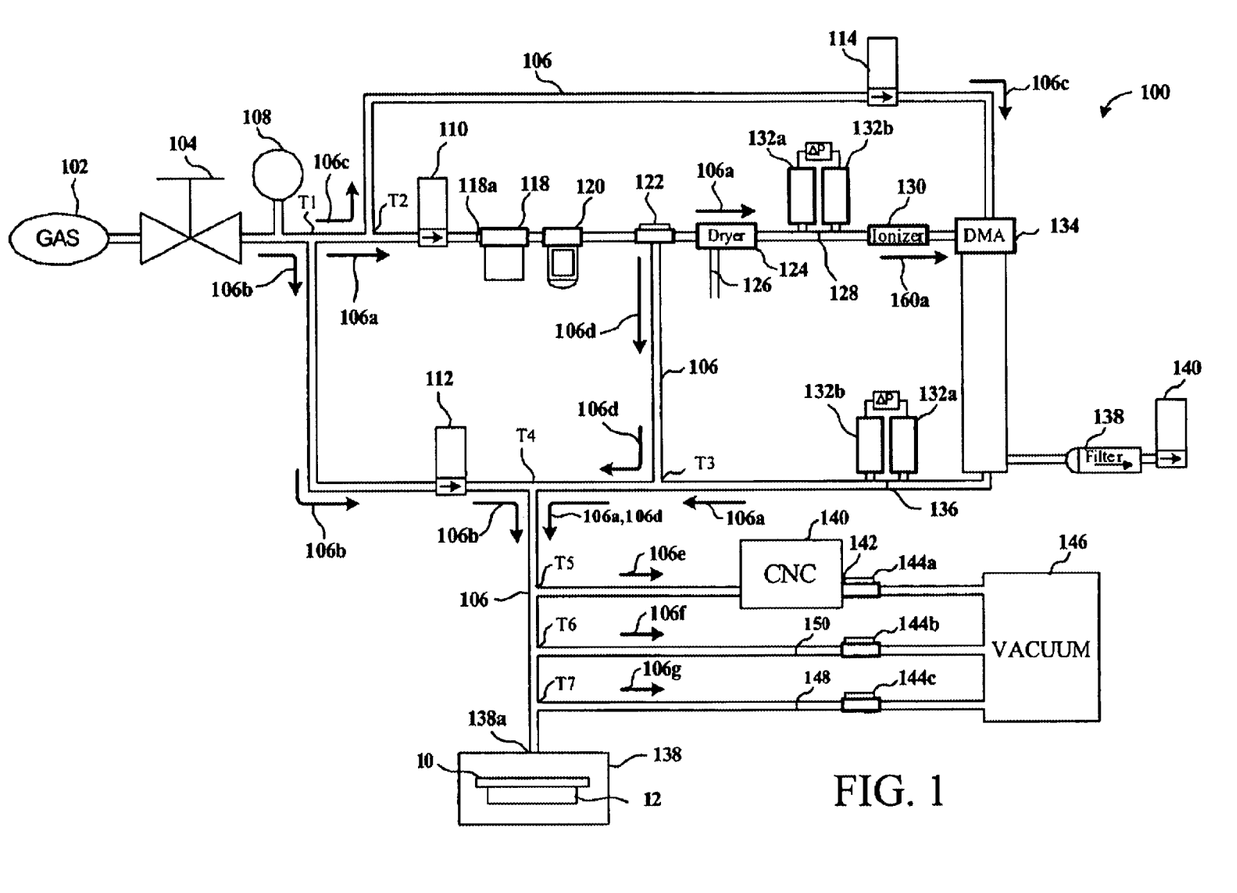
FIG. 1 is a simplified schematic diagram of an exemplary particle deposition system in accordance with one embodiment of the present invention.

FIG. 1 is a simplified schematic diagram of an exemplary particle deposition system in accordance with one embodiment of the present invention. As shown in FIG. 1, particle deposition system 100 is coupled in flow communication with gas source 102 via pressure valve 104. By way of example, gas source 102 may be a source of nitrogen or compressed dry air (CDA). When pressure valve 104 is open, gas from gas source 102 flows into conduit system 106. Pressure gauge 108, which is disposed just after pressure valve 104, monitors the gas pressure in conduit system 106. Conduit system 106 includes a branch T1 that directs the gas flow along flow paths 106a and 106b. Flow path 106a directs the gas flow toward atomizer flow controller 110 and flow path 106b directs the gas flow toward makeup flow controller 112. Conduit system 106 includes another branch T2 that directs a portion of the gas flow from flow path 106a along flow path 106c, which directs the gas flow toward sheath flow controller 114.

The gas flow passing by branches T1 and T2 along flow path 106a enters atomizer flow controller 110, which may be any suitable flow controller that can be controlled to allow the gas to flow therethrough at a desired rate. In one embodiment, the gas flow through atomizer flow controller 110 is in the range from about 5 liters/minute to 6 liters/minute. The gas flows from atomizer flow controller 110 into atomizer 118, which includes orifice 118a. The size of orifice 118a is selected to allow a desired amount of gas to flow therethrough. As is well known to those skilled in the art, atomizer 118, which includes a bowl containing deionized water (DIW) and particles, introduces wet particles into the gas flow and thereby generates an aerosol flow. When particle deposition system 100 is being used to make standards, the particles provided in atomizer 118 are typically polystyrene latex (PSL) particles having a uniform shape and a uniform particle size. It will be apparent to those skilled in the art that particle deposition system 100 also may be used to deposit other man made particles as well as naturally occurring particles that have nonuniform shapes and nonuniform particle sizes. By way of example, the naturally occurring particles may be particles of silicon, tungsten, copper, or aluminum oxide.

The aerosol flow leaving atomizer 118 flows through water trap 120, which is a safety device that captures any excess water that is drawn into conduit system 106. After passing through water trap 120, the aerosol flow flows into three-way solenoid 122, which can be controlled to direct the aerosol flow along either flow path 106a or flow path 106d. In one embodiment, three-way solenoid 122 is controlled based on the size of the particles in the aerosol flow as will be described in more detail below. Those skilled in the art will recognize that other suitable flow switching devices, e.g., valves, may be used in place of three-way solenoid 122.

When the three-way solenoid 122 directs the aerosol flow along flow path 106a, the aerosol flow flows into dryer 124, which performs two functions. First, dryer 124 dries the relatively small particles in the aerosol flow to ensure that such particles are not encapsulated in water droplets. If the particles are encapsulated in water droplets, then they may behave like larger particles. This is undesirable because it may prevent properly sized particles from being passed through a differential mobility analyzer (DMA), as described later. Second, dryer 124 exhausts some of the aerosol flow to atmosphere via orifice 126 to minimize the flow into the DMA. The aerosol flow leaving dryer 124 flows through orifice 128 and into ionizer 130. The size of orifice 128 is selected to allow a desired amount of gas to flow therethrough. Pressure sensors 132*a* and 132*b* are situated on opposing sides of orifice 128 so that the pressure differential, $\Delta P$, across this orifice can be determined. Using the pressure differential across orifice 128 determined by pressure sensors 132*a* and 132*b* and the size of the orifice, a computer can calculate the aerosol flow through the orifice. Ionizer 130 changes the charge distribution of the particles in the aerosol flow before the aerosol flow reaches DMA 134, which passes mostly singly charged particles having a certain size. The use of ionizer 130 is necessary because the particles in the aerosol flow are highly charged when they leave atomizer 118. As is well known to those skilled in the art, ionizer 130 includes a radioactive source that introduces charged ions into the aerosol flow. The aerosol flow leaving ionizer 130 includes a reasonable fraction of singly charged particles that can be handled by DMA 134.

The aerosol flow leaving ionizer 130 flows into DMA 134. A flow of clean sheath gas also flows into DMA 134 along flow path 106*c*. Sheath flow controller 114, which may be any suitable flow controller, controls the flow rate of the clean sheath gas into DMA 134. DMA 134 may be any suitable commercially available DMA and those skilled in the art are familiar with the structure and operation of such DMAs. In short, DMA 134 includes an outer tube and an inner rod, which has a slit toward the bottom thereof (neither the outer tube nor the inner rod is shown in FIG. 1). A negative voltage is applied to the inner rod and, consequently, positively charged particles are attracted toward the inner rod. On the other hand, negatively charged particles are repelled toward the outer tube. At the same time, the laminar flow of clean sheath gas moves the particles through DMA 134, i.e., from the top of the DMA to the bottom of the DMA. The smaller, positively charged particles are attracted to the inner rod while the larger particles are impacted out. As is well known to those skilled in the art, only particles having the diameter of interest will pass through the slit. The aerosol flow containing particles that have passed through the slit exits the bottom of DMA 134 and flows toward orifice 136.

The excess gas flow exits the bottom of DMA 134 and any excess particles in the excess gas flow are captured in filter 138 so that they can be disposed of as waste. The excess gas flow flows from filter 138 into excess flow controller 140 and is then discharged to the atmosphere. Excess flow controller 140 may be any suitable flow controller that can control the flow rate of the excess gas flow out of DMA 134. In one embodiment, excess flow controller 140 controls the flow rate of the excess gas flow so that this flow rate matches the flow rate of the sheath gas flowing into DMA 134 along flow path 106*c*.

As noted above, the aerosol flow containing particles that have passed through the slit, i.e., the sized particles that will be used in the deposition, exits the bottom of DMA 134 and flows into orifice 136. The size of orifice 136 is selected to allow a desired amount of gas to flow therethrough. Pressure sensors 132*a* and 132*b* are situated on opposing sides of orifice 136 so that the pressure differential, $\Delta P$, across this orifice can be determined. Using the pressure differential across orifice 136 determined by pressure sensors 132*a* and 132*b* and the size of the orifice, a computer can calculate the aerosol flow through the orifice. After passing through orifice 136, the aerosol flow continues to flow along flow path 106*a* toward deposition chamber 138. Once the aerosol flow flows by branch T3, branch T4 directs the aerosol flow toward deposition chamber 138. Branch T4 also directs the gas flow flowing along flow path 106*b* toward deposition chamber 138. Makeup flow controller 112, which may be any suitable flow controller, controls the flow rate of the gas flow along flow path 106*b*. In one embodiment, makeup flow controller 112 controls the flow rate of the gas flow along flow path 106*b* so that the combination of this flow rate and the flow rate of the aerosol flow exiting DMA 134 slightly exceeds the flow rate that is removed from the aerosol gas flow for purposes of particle counting, as will be explained in more detail later.

The combined aerosol flow, which includes the aerosol flow from flow path 106*a* and the gas flow from flow path 106*b*, flows from branch T4 toward deposition chamber 138. When a deposition is in progress, a vacuum causes branch T5 to direct a portion of the combined aerosol flow toward condensation nucleus counter (CNC) 140 along vacuum flow path 106*e*. CNC 140 may be any suitable commercially available CNC. It will be apparent to those skilled in the art that other suitable particle counters also may be used. As is well known to those skilled in the art, CNC 140 counts the particles in the combined aerosol flow and thereby enables a deposition process to be stopped when a desired particle count has been reached. After passing through CNC 140, the combined aerosol gas flow flows through orifice 142 and two-way solenoid 144*a*, which is coupled in flow communication with vacuum system 146. Two-way solenoid 144*a* functions as on/off switch for vacuum system 146. Those skilled in the art will recognize that other suitable flow switching devices, e.g., valves, may be used in place of two-way solenoid 144*a* (as well as two-way solenoids 144*b* and 144*c* described below). When a deposition is in progress, two-way solenoid 144*a* is open so that the vacuum draws a portion of the combined aerosol flow into vacuum flow path 106*e*. In one embodiment, the flow rate of the combined aerosol flow through CNC 140 is substantially constant because orifice 142 is run at critical pressure.

The remaining portion of the combined aerosol flow. i.e., the portion that is not drawn into vacuum flow path 106*e*, flows into deposition chamber 138 via aerosol inlet 138*a*. By way of example, in one embodiment, the aerosol flow exiting DMA 134 has a flow rate of about 0.5 liter/minute and makeup flow controller 112 controls the gas flow rate in flow path 106*b* such that this flow rate is about 2.4 liters/minute. Thus, the flow rate of the combined aerosol flow is about 2.9 liters/minute. In this embodiment, CNC 140 removes about 2.8 liters/minute from the combined aerosol flow for purposes of particle counting. Consequently, the remaining portion of the combined aerosol flow that flows into deposition chamber 138 has a flow rate of about 0.1 liter/minute. It is to be understood that the flow into the deposition chamber may have a flow rate higher than 0.1 liter/minute, but such a flow rate is less preferred because it may cause the particles to spread out beyond the desired spot diameter.

The particles in the aerosol flow entering deposition chamber 138 are deposited onto substrate 10, which is supported on support member 12. By way of example, substrate 10 may be a semiconductor wafer. Support member 12 may be any suitable support member, but preferably is a support member that is capable of moving substrate 10 within deposition chamber 138. In one embodiment, support member 12 is capable of moving substrate 10 in a linear fashion as well as a rotary fashion. For a so-called full deposition, i.e., a deposition on the full surface of substrate 10, the substrate is typically disposed 3 to 4 inches below aerosol inlet 138a. For a so-called spot deposition, i.e., a deposition on a small portion of substrate 10, a nozzle (not shown in FIG. 1) is disposed in deposition chamber 138 in flow communication with aerosol inlet 138a and the substrate is typically disposed about 0.25 inch below the outlet of the nozzle.

When DMA 134 is being used to size the particles, the deposition process is stopped using a vacuum that causes branch T7 to direct the remaining portion of the combined aerosol flow along vacuum flow path 106g. The vacuum is controlled by two way solenoid 144c, which is coupled in flow communication with vacuum system 146 and functions as on/off switch for the vacuum system. Orifice 148 is situated between branch 17 and two-way solenoid 144c. In one embodiment, the size of orifice 148 is selected so that the flow rate through this orifice slightly exceeds the flow rate of the remaining portion of the combined aerosol flow into deposition chamber 138. Thus, when two-way solenoid 144c is open, the vacuum draws the entirety of the remaining portion of the combined aerosol flow into vacuum flow path 106g. Consequently, none of this flow enters deposition chamber 138.

The foregoing description describes the gas flow through particle deposition system 100 when the system is being run in DMA mode, i.e., when DMA 134 is being used to size the particles that will enter deposition chamber 138. Particle deposition system 100 also may be run in bypass mode, however. Bypass mode enables particle deposition system 100 to be used to deposit particles without passing the particles through the DMA. By way of example, bypass mode may be used to deposit relatively large particles that cannot be sized by DMA 134. In one exemplary embodiment, particle deposition system 100 is run in DMA mode when the aerosol flow includes relatively small particles, e.g., particles having a particle size up to 1.5 microns, and the particle deposition system is run in bypass mode when the aerosol flow includes relatively large particles, e.g., particles having a particle size larger than 1.5 microns. It will be apparent to those skilled in the art that the particle deposition system can be run in DMA mode using particles larger than 1.5 microns when the DMA is capable of filtering such larger particles. To switch particle deposition system 100 into bypass mode, three-way solenoid 122 is activated to direct the aerosol flow along flow path 106d. Branch T3 directs the aerosol flow toward branch T4, which in turn directs the aerosol flow toward deposition chamber 138. Branch T4 also directs the gas flow flowing along flow path 106b toward deposition chamber 138. In one embodiment, makeup flow controller 112 controls the flow rate of the gas flow along flow path 106b so that the combination of this flow rate and the flow rate of the aerosol flow from flow path 106d slightly exceeds the flow rate that is removed from the aerosol gas flow by CNC 140, as described above.

The combined aerosol flow, which includes the aerosol flow from flow path 106d and the gas flow from flow path 106b, flows from branch T4 toward deposition chamber 138. As described above, when a deposition is in progress, a vacuum causes branch T5 to direct a portion of the combined aerosol flow toward CNC 140 along vacuum flow path 106e.

The remaining portion of the combined aerosol flow, i.e., the portion that is not drawn into vacuum flow path 106e, flows into deposition chamber 138 via aerosol inlet 138a. In bypass mode, the deposition process is stopped using a vacuum that causes branch T6 to direct the remaining portion of the combined aerosol flow along vacuum flow path 106f. The vacuum is controlled by two-way solenoid 144b, which is coupled in flow communication with vacuum system 146 and functions as on/off switch for the vacuum system. Orifice 150 is situated between branch T6 and two-way solenoid 144b. In one embodiment, the size of orifice 150 is selected so that the flow rate through this orifice slightly exceeds the flow rate of the remaining portion of the combined aerosol flow into deposition chamber 138. Thus, when two-way solenoid 144b is open, the vacuum draws the entirety of the remaining portion of the combined aerosol flow into vacuum flow path 106f. Consequently, none of this flow enters deposition chamber 138.

Figure 2:
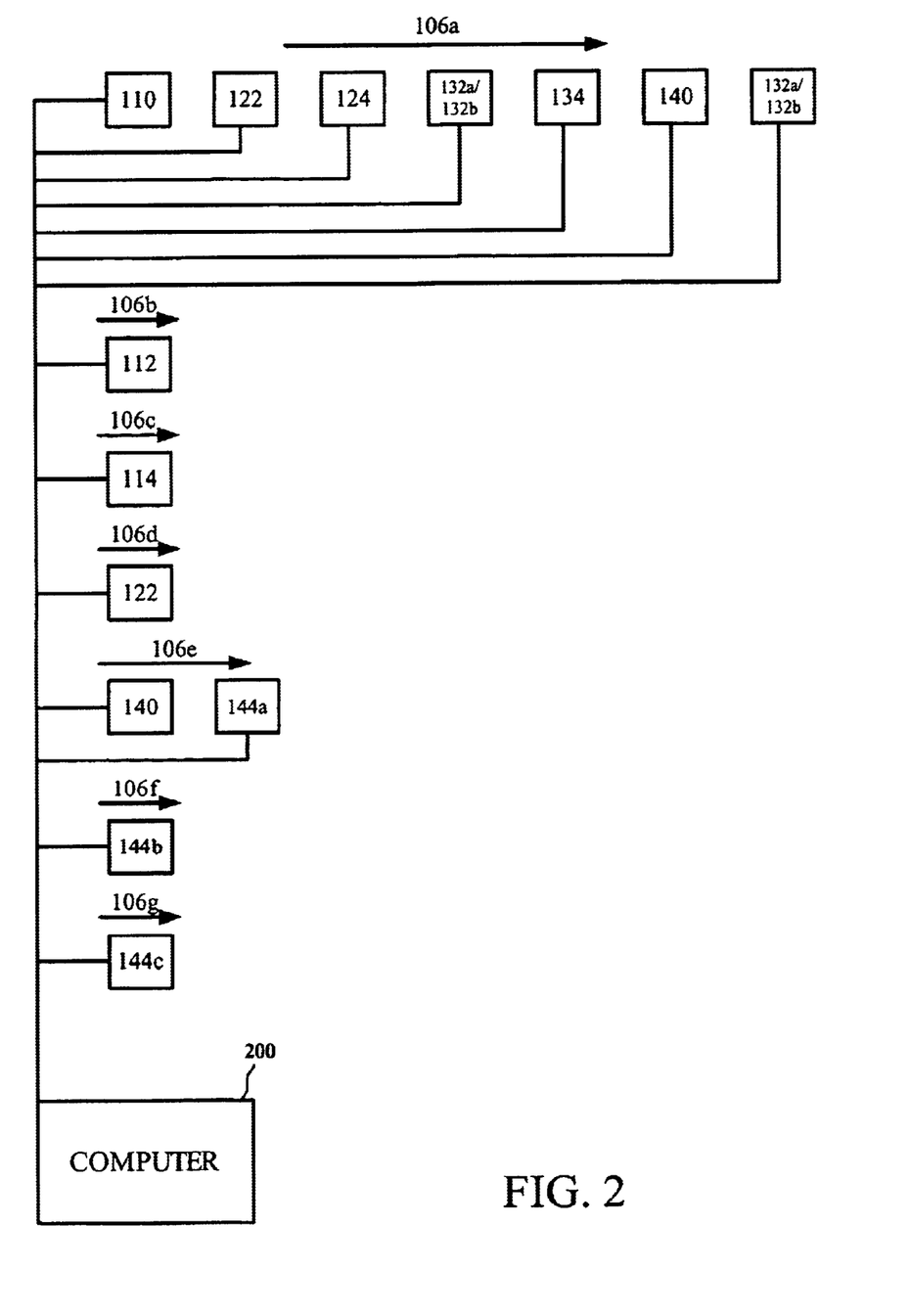
FIG. 2 is a block diagram that illustrates how a computer can be used to control the operation of the exemplary particle deposition system shown in FIG. 1 using real time feedback.

FIG. 2 is a block diagram that illustrates how a computer can be used to control the operation of particle deposition system 100 shown in FIG. 1 using real time feedback. As shown in FIG. 2, along flow path 106a, computer 200 is coupled to atomizer flow controller 110, three-way solenoid 122, dryer 124, the first pair of pressure sensors 132a and 132b (located before DMA 134), DMA 134, excess flow controller 140, and the second pair of pressure sensors (located after DMA 134). Along flow path 106b, computer 200 is coupled to makeup flow controller 112. Along flow path 106c, computer 200 is coupled to sheath flow controller 114. Along flow path 106d, computer 200 is coupled to three-way solenoid 122. Along vacuum flow path 106e, computer 200 is coupled to CNC 140 and two-way solenoid 144a. Along vacuum flow path 106f, computer 200 is coupled to two-way solenoid 144b. Finally, along vacuum flow path 106g, computer 200 is coupled to two-way solenoid 144c.

Computer 200 sets and reads back the flows through atomizer flow controller 110, makeup flow controller 112, sheath flow controller 114, and excess flow controller 140. To control whether particle deposition system 100 operates in DMA mode or bypass mode, computer 200 sends a control signal to three-way solenoid 122 that causes this solenoid to direct the flow along the desired flow path, i.e., flow path 106a or flow path 106d. Computer 200 reads back the temperature within dryer 124. To determine the particle input into DMA 134, computer 200 reads back the pressures detected by the first pair of pressure sensors 132a, 132b, and determines the pressure differential, ΔP, across orifice 128 (see FIG. 1). Using this pressure differential and the size of orifice 128, computer 200 calculates the aerosol flow through orifice 128. To determine the particle flow out of DMA 134, computer 200 reads back the pressures detected by the second pair of pressure sensors 132a, 132b, and determines the pressure differential, ΔP, across orifice 136 (see FIG. 1). Using this pressure differential and the size of orifice 136, computer 200 calculates the aerosol flow through orifice 136.

To control the size of the particle passed by DMA 134, computer 200 controls the voltage applied to the inner rod of the DMA. The applied voltage required for DMA 134 to pass particles having a specific size is a function of the flows into and out of the DMA. Accordingly, computer 200 periodically, e.g., every few seconds, uses an equation known to those skilled in the art to calculate the voltage required for DMA 134 to pass the desired particle size based on the current flows into and out of the DMA, i.e., the aerosol flow through orifice 128 before the DMA, the flow through sheath flow controller 114, the flow through orifice 136 after the DMA, and the flow through excess flow controller 140. Computer 200 then compares the calculated voltage with the voltage currently being applied to DMA 134 and, if necessary, adjusts the voltage being applied to the DMA. By controlling the voltage applied to DMA 134 in this manner, computer 200 ensures that the passed particle size remains constant during the deposition process.

Regarding particle counting, computer 200 sets the particle counting parameters used by CNC 140 and reads back the particle count from the CNC. Whenever the particle counter is put into operation, computer 200 sends a control signal to two-way solenoid 144a that opens this solenoid and thereby puts vacuum system 146 (see FIG. 1) in flow communication with vacuum flow path 106e. Computer 200 also sends control signals to two-way solenoids 144b and 144c. When particle deposition system 100 is operating in DMA mode, two-way solenoid 144b is closed so that vacuum flow path 106f is not in flow communication with vacuum system 146. During the initial stabilization of particle deposition system 100 in DMA mode, computer 200 keeps two-way solenoid 144c open so that vacuum flow path 106g is in flow communication with vacuum system 146. As described above, this causes the aerosol flow to be drawn into the vacuum system via vacuum flow path 106g. Whenever particles are to be deposited into deposition chamber 138 (see FIG. 1), computer 200 closes two-way solenoid 144c to interrupt the flow communication between vacuum flow path 106g and vacuum system 146. As described above, this causes the aerosol flow to enter deposition chamber 138.

When particle deposition system 100 is operating in bypass mode, two-way solenoid 144c is closed so that vacuum flow path 106g is not in flow communication with vacuum system 146. During initial stabilization of particle deposition system 100 in bypass mode, computer 200 keeps two-way solenoid 144b open so that vacuum flow path 106f is in flow communication with vacuum system 146. As described above, this causes the aerosol flow to be drawn into the vacuum system via vacuum flow path 106f. Whenever particles are to be deposited into deposition chamber 138 (see FIG. 1), computer 200 closes two-way solenoid 144b to interrupt the flow communication between vacuum flow path 106f and vacuum system 146. As described above, this causes the aerosol flow to enter deposition chamber 138.

In one embodiment, computer 200 is programmed to display a user interface that enables the user to control the entire deposition process. Through the user interface, the user can input the desired particle count and particle size and can monitor the particle count as the deposition proceeds. In addition, by clicking the appropriate button, the user can pause or terminate the deposition process. After each deposition, the user interface prompts the user to determine whether additional depositions are to be conducted. By way of example, another deposition of the same particle size may be conducted at a different spot on the substrate or on a different substrate. Alternatively, the deposition may be stopped and the particle deposition system can be configured to deposit particles having a different size. Upon reading this specification, those skilled in the art will be able to formulate an appropriate user interface for computer 200.

Referring now to FIG. 1, once a user has input the desired deposition parameters for a deposition in DMA mode, particle deposition system 100 undergoes an initial stabilization procedure in which the system stabilizes the flows and sets the voltage being applied to DMA 134. During the initial stabilization procedure, the aerosol flow flows in vacuum system 146 via vacuum flow path 106g. Once particle deposition system 100 has stabilized, computer 200 automatically closes two-way solenoid 144c to interrupt the flow communication between vacuum flow path 106g and vacuum system 146 and thereby divert the aerosol flow into deposition chamber 138. As described above, CNC 140 counts the particles that are deposited onto substrate 10 during the deposition process. When the specified number of particles ("the stop count") has been deposited onto substrate 10, computer 200 automatically opens two-way solenoid 144c to divert the aerosol flow back into vacuum system 146. If desired, a user may pause the deposition process before the stop count is reached to, e.g., change the stop count. In one embodiment, this is accomplished by having the user click on a "pause deposition" button displayed by the user interface. When a user clicks on the "pause deposition" button, computer 200 opens two-way solenoid 144c to divert the aerosol flow back into vacuum system 146 so that no particles enter deposition chamber 138 while the deposition process is paused.

Figure 3:
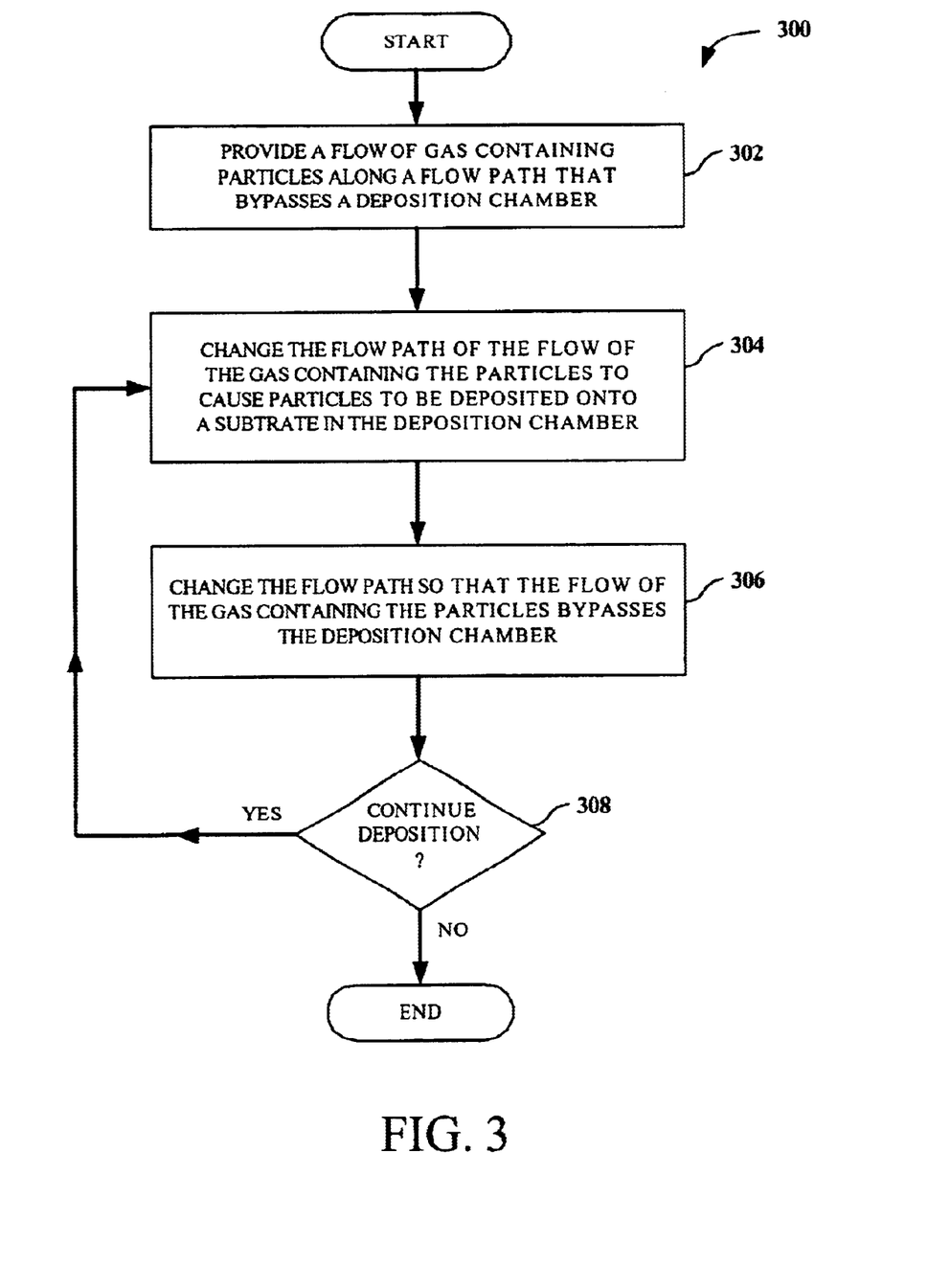
FIG. 3 is a flow chart diagram that illustrates the method operations performed in depositing particles onto a substrate in accordance with one embodiment of the present invention.

FIG. 3 is a flow chart diagram 300 that illustrates the method operations performed in depositing particles onto a substrate in accordance with one embodiment of the present invention. The method begins in operation 302 in which a flow of gas containing particles, i.e., an aerosol flow, is provided along a flow path that bypasses a deposition chamber. In one embodiment, the flow path directs the flow of the gas containing the particles into a vacuum. By way of example, this may be accomplished using a particle deposition system having the configuration shown in FIG. 1. As deposition chamber 138 shown in FIG. 1 is in flow communication with vacuum system 146, the vacuum should be configured to prevent the flow of the gas containing the particles from entering the deposition chamber without drawing any significant amount of air from the deposition chamber. As used herein, the phrase "significant amount of air" means an amount of air sufficient to cause contamination to be introduced onto a substrate in the deposition chamber. To avoid contaminating the substrate, in one embodiment, the flow to the vacuum matches or slightly exceeds the flow of the flow of gas containing the particles. It will be apparent to those skilled in the art that the flow path does not have to direct the flow of the gas containing the particles into a vacuum. By way of example, the flow path may bypass the deposition chamber by directing the flow of the gas containing the particles into a waste receptacle.

In operation 304, the flow path of the flow of gas containing the particles is changed so that this flow causes particles to be deposited onto a substrate in the deposition chamber. In one embodiment, the flow of the gas containing the particles is diverted from the vacuum into the deposition chamber by interrupting the flow communication between the vacuum and the flow of the gas containing the particles. By way of example, this may be accomplished by controlling a valve, e.g., a solenoid, to take the vacuum out of flow communication with the flow of the gas containing the particles. It will be apparent to those skilled in the art that the flow path of the gas containing the particles may be changed using a mechanism other than a vacuum. By way of example, the flow path may be changed by controlling a suitable valve, e.g., a three-way valve, or by directing a pressurized stream of air or other suitable gas at the flow of gas containing the particles.

In operation 306, the flow path is changed so that the flow of the gas containing the particles bypasses the deposition chamber. This may be done to pause a deposition process, e.g., to change the stop count or to move the substrate into a different position for another spot deposition, or to stop a deposition process, e.g., when the number of particles deposited has reached the stop count. When a vacuum is used to control the flow path, the flow path may be changed by putting the flow of the gas containing the particles back into flow communication with the vacuum. Alternatively, the flow path may be changed by controlling a suitable valve or by stopping the pressurized stream of air or other suitable gas.

The method then proceeds to decision operation 308 in which it is determined whether deposition is to be continued. By way of example, the deposition process may be continued either to finish a deposition that was paused or to conduct additional spot depositions at different locations on the same substrate. If it is determined in decision operation 308 that deposition is to be continued, then the method proceeds repeats operations 304 and 306 and returns back to decision operation 308. Operations 304 and 306 may be repeated as many times as desired, e.g., to make multiple spot depositions on the same substrate. Once it is determined in decision operation 308 that deposition is not to be continued, the method is done.

Figure 4:
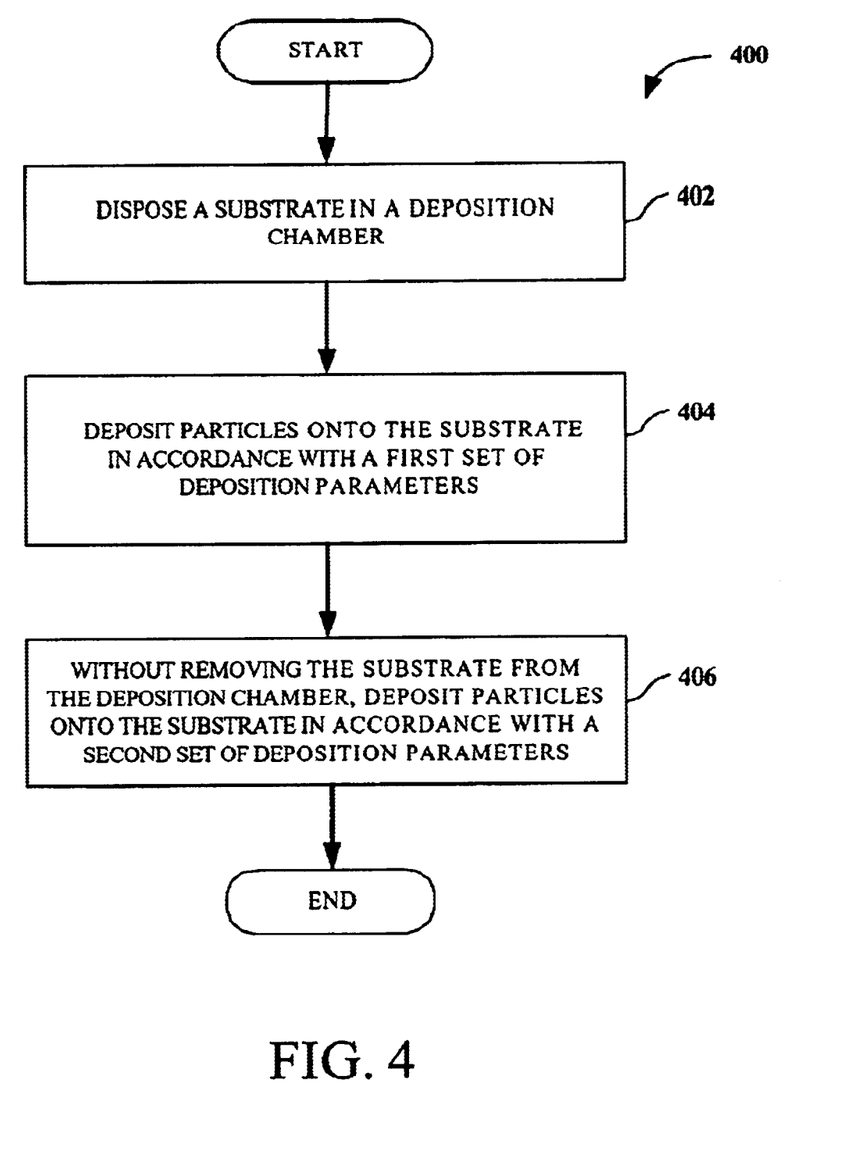
FIG. 4 is a flow chart diagram that illustrates the method operations performed in depositing particles onto a substrate in accordance with another embodiment of the present invention.

FIG. 4 is a flow chart diagram 400 that illustrates the method operations performed in depositing particles onto a substrate in accordance with another embodiment of the present invention. The method begins in operation 402 in which a substrate, e.g., a semiconductor wafer, is disposed in a deposition chamber. In operation 404, particles are deposited onto the substrate in accordance with a first set of deposition parameters. By way of example, the first set of deposition parameters may include a specific particle size and a specific spot location on the substrate for the deposition. The particles may be deposited onto the substrate in accordance with the first set of deposition parameters using the method described above with reference to FIG. 3.

In operation 406, without removing the substrate from the deposition chamber, particles are deposited onto the substrate in accordance with a second set of deposition parameters. The substrate does not have to be removed from the deposition chamber before the second deposition because no unwanted particles are introduced into the deposition chamber during the first deposition. In contrast, in conventional particle deposition systems, the substrate must be removed from the deposition chamber so that unwanted particles can be purged from the deposition chamber. In one embodiment, the second set of deposition parameters includes the same particle size as the first set of deposition parameters and a different spot location on the substrate than in the first set of deposition parameters. In another embodiment, both the particle size and the spot location on the substrate in the second set of deposition parameters are different from those in the first set of deposition parameters. The particles may be deposited onto the substrate in accordance with the second set of deposition parameters using the method described above with reference to FIG. 3. Once the particles have been deposited onto the substrate in accordance with the second set of deposition parameters, the method is done; however, it will be apparent to those skilled in the art that additional depositions may be conducted if desired.

Figure 5:
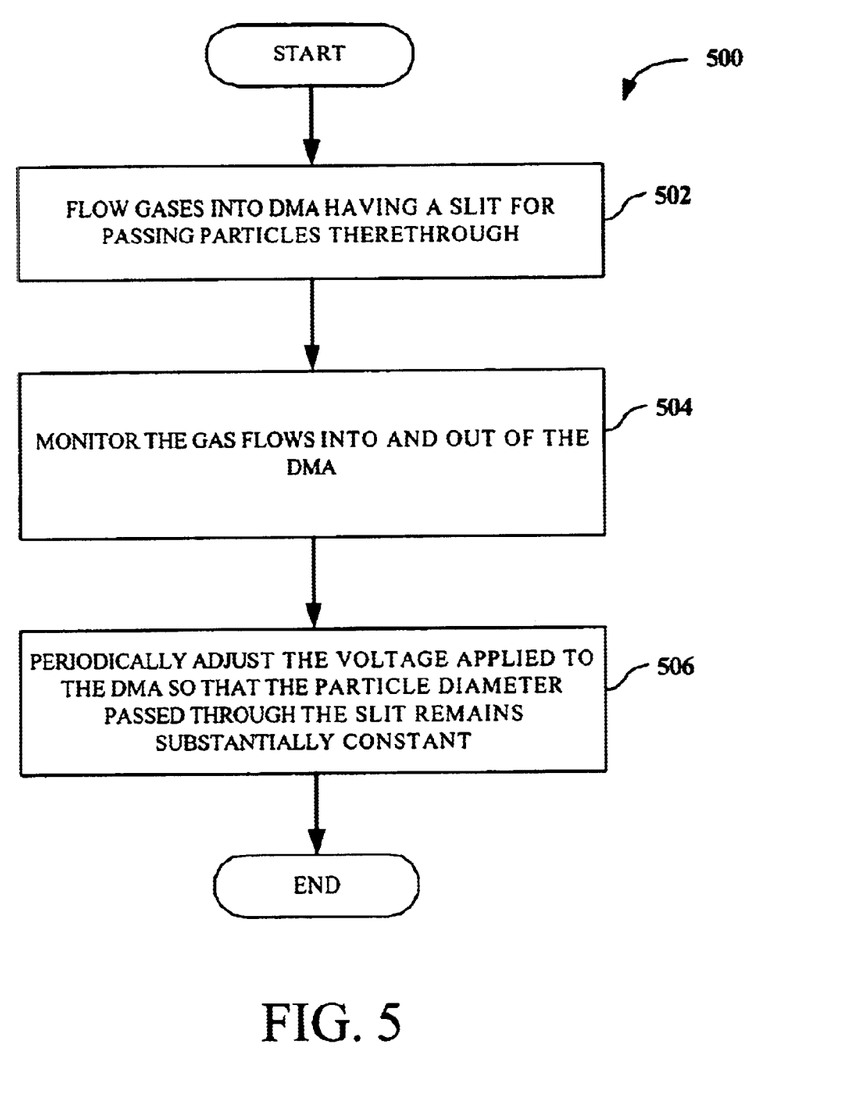
FIG. 5 is a flow chart diagram that illustrates the method operations performed in maintaining particle diameter during deposition of particles in accordance with one embodiment of the present invention.

FIG. 5 is a flow chart diagram 500 that illustrates the method operations performed in maintaining particle diameter during deposition of particles in accordance with one embodiment of the present invention. The method begins in operation 502 in which gases are flowed into a differential mobility analyzer (DMA) having a slit for passing particles therethrough. At least one of the gases flowing into the DMA contains. particles to be sized by the DMA. The DMA may be any suitable commercially available DMA and operation 502 may be implemented in any system that contains such a DMA. In one embodiment, operation 502 is implemented in a particle deposition system that is comparable to particle deposition system 100 shown in FIG. 1. In operation 504, the gas flows into and out of the DMA are monitored. In the embodiment in which operation 502 is implemented in a particle deposition system that is comparable to that shown in FIG. 1, the monitored gas flows include the aerosol flow through orifice 128 before the DMA, the flow through sheath flow controller 114, the flow through orifice 136 after the DMA, and the flow through excess flow controller 140. In one embodiment, the aerosol flow through orifice 128 and the aerosol flow through orifice 136 are determined by measuring the pressure differential across the respective orifices. Alternatively, the aerosol flows into and out of the DMA may be monitored using mass flow controllers.

In operation 506, the voltage applied to the DMA is periodically adjusted so that the particle diameter passed through the slit in the DMA remains substantially constant. As described above, the voltage required for the DMA to pass particles having a specific size is a function of the flows into and out of the DMA. In one embodiment, a computer or other suitable signal processor adjusts the voltage applied to the DMA based on the gas flows into and out of the DMA. By way of example, the computer can accomplish this by periodically, e.g., every few seconds, using an equation known to those skilled in the art to calculate the voltage required for the DMA to pass the desired particle size based on the current flows into and out of the DMA. The computer then compares the calculated voltage with the voltage currently being applied to the DMA and makes any necessary adjustments to the voltage being applied to the DMA. By controlling the voltage applied to the DMA in this manner, it is ensured that the passed particle size remains substantially constant during the deposition process. The periodic voltage adjustments are preferably carried out during the entire time particles are deposited onto the substrate. Once the deposition process stops, operation 506 is finished and the method is done.

The present invention advantageously enables particles having a constant particle diameter to be deposited onto a substrate in a deposition chamber without introducing unwanted particles in the deposition chamber. This avoids the need to purge the deposition chamber between depositions. Consequently, multiple depositions can be made on a substrate without removing the substrate from the deposition chamber. By minimizing the handling of the substrate required for deposition, the present invention significantly decreases the time required to produce standards having multiple depositions thereon. It also minimizes the opportunity for contamination to be introduced onto the substrate during the deposition process.

In summary, the present invention provides a particle deposition system, a method for depositing particles on a substrate, and a method for maintaining particle diameter during deposition of particles on a substrate. The invention has been described herein in terms of several exemplary embodiments. Other embodiments of the invention will be apparent to those skilled in the art from consideration of the specification and practice of the invention. By way of example, as described above, the principles of the invention may be implemented without using a vacuum as shown in FIG. 1. The embodiments and preferred features described above should be considered exemplary, with the scope of the invention being defined by the appended claims and their equivalents.

What is claimed is:

1. A particle deposition system, comprising:

a deposition chamber having an inlet;

a conduit coupled to the inlet of the deposition chamber, the conduit being in flow communication with a source of gas containing particles, and the conduit having a first branch and a second branch;

a particle counter disposed in the first branch of the conduit;

an orifice disposed in the second branch of the conduit; and a vacuum coupled in flow communication with the first branch of the conduit and the second branch of the conduit.

2. The system of claim 1, wherein the first branch of the conduit is closer to the source of gas containing particles than the second branch of the conduit.

3. The system of claim 1, further comprising:

a first solenoid disposed in the first branch of the conduit between the particle counter and the vacuum; and a second solenoid disposed in the second branch of the conduit between the orifice and the vacuum.

4. The system of claim 3, further comprising:

an orifice disposed in the first branch of the conduit between the particle counter and the first solenoid.

5. The system of claim 1, wherein the source of the gas containing the particles is an atomizer.

6. The system of claim 5, further comprising a differential mobility analyzer in flow communication with the atomizer.

7. The system of claim 6, further comprising an orifice disposed before the differential mobility analyzer and an orifice disposed after the differential mobility analyzer.

8. The system of claim 7, further comprising a first pair of pressure sensors for measuring a pressure differential across the orifice disposed before the differential mobility analyzer and a second pair of pressure sensors for measuring a pressure differential across the orifice disposed after the differential mobility analyzer.

9. The system of claim 1, wherein the conduit has a third branch, the third branch being in flow communication with the vacuum.

10. The system of claim 9, further comprising:

an orifice disposed in the third branch of the conduit.

11. The system of claim 10, further comprising:

a third solenoid disposed in the third branch of the conduit between the orifice and the vacuum.

12. The system of claim 1, wherein the conduit is in flow communication with a source of makeup gas.

13. A particle deposition system, comprising:

an atomizer for providing a flow of gas containing particles;

a flow control device coupled in flow communication with the atomizer;

a differential mobility analyzer coupled in flow communication with the flow control device; and a deposition chamber coupled in flow communication with the flow control device and the differential mobility analyzer, wherein when the particles in the flow of the gas containing the particles are to be filtered by the differential mobility analyzer, the flow control device directs the flow of the gas containing the particles toward the differential mobility analyzer, and when the particles in the flow of the gas containing the particles are not to be filtered by the differential mobility analyzer, the flow control device directs the flow of the gas containing the particles toward the deposition chamber.

14. The particle deposition system of claim 13, wherein the flow control device is a three-way solenoid.

15. The particle deposition system of claim 13, wherein when the particles in the flow of the gas containing the particles have a size that is not larger than 1.5 microns, the flow control device directs the flow of the gas containing the particles toward the differential mobility analyzer, and when the particles in the flow of the gas containing the particles have a size that is larger than 1.5 microns, the flow control device directs the flow of the gas containing the particles toward the deposition chamber.

* * * * *